US007795406B2

(12) United States Patent
Wittig et al.

(10) Patent No.: US 7,795,406 B2
(45) Date of Patent: Sep. 14, 2010

(54) AGENT FOR TREATING LEISHMANIA INFECTIONS

(75) Inventors: Burghardt Wittig, Berlin (DE); Laura Fuertes-López, Madrid (ES); Marcos Timón-Jiménez, San Lorenzo de El Escorial (ES)

(73) Assignee: Mologen AG, Berlin (DE)

( * ) Notice: Subject to any disclaimer, the term of this patent is extended or adjusted under 35 U.S.C. 154(b) by 0 days.

(21) Appl. No.: 11/291,098

(22) Filed: Nov. 30, 2005

(65) Prior Publication Data
US 2006/0194753 A1 Aug. 31, 2006

Related U.S. Application Data

(63) Continuation-in-part of application No. PCT/DE2004/002383, filed on Oct. 22, 2004.

(30) Foreign Application Priority Data

Oct. 24, 2003 (EP) ............................. 03090368.6

(51) Int. Cl.
C07H 21/02 (2006.01)
C07H 21/04 (2006.01)
(52) U.S. Cl. ..................... 536/23.1; 536/23.4; 536/23.7
(58) Field of Classification Search ................ 536/23.1, 536/23.4, 23.7
See application file for complete search history.

(56) References Cited

U.S. PATENT DOCUMENTS

| 6,451,563 | B1 * | 9/2002 | Wittig et al. ............... 435/91.5 |
| 6,458,359 | B1 * | 10/2002 | Bedate et al. ............. 424/192.1 |
| 6,962,704 | B2 * | 11/2005 | Bedate et al. ............. 424/184.1 |
| 2002/0081320 | A1 | 6/2002 | Reed et al. |
| 2004/0235771 | A1 | 11/2004 | Moreno-Lopez et al. |

FOREIGN PATENT DOCUMENTS

| EP | 0 941 318 B1 | 1/2001 |
| EP | 1 196 178 B1 | 6/2004 |
| WO | WO 01/07055 A1 | 2/2001 |

OTHER PUBLICATIONS

Planelles et al., DNA immunization with Trypanosoma cruzi HSP70 fused to the KMP11 protein elicits a cytotoxic and humoral immune response against the antigen and leads to protection. Infect Immun. 69(10):6558-63, 2001.*
Campos-Neto et al., Vaccination with plasmid DNA encoding TSA/LmSTI1 leishmanial fusion proteins confers protection against Leishmania major infection in susceptible BALB/c mice. Infect Immun. 70(6): 2828-36, 2002.*
Yao et al., The major surface protease (MSP or GP63) of Leishmania sp. Biosynthesis, regulation of expression, and function, Mol Biochem Parasitol. 132(1): 1-16, 2003.*
Miller and Vile, Targeted vectors for gene therapy, FASEB J. 9(2): 190-9, 1995.*

Deonarain, Ligand-targeted receptor-mediated vectors for gene delivery, Exp. Opin. Ther. Patents 8(1): 53-69, 1998; Ashley Publications Ltd. ISSN 1354-3776.*
Verma and Somia, Gene therapy—promises, problems and prospects, Nature 389: 239-42, 1997.*
Crystal, Transfer of genes to humans: early lessons and obstacles to success, Science 270: 404-10, 1995.*
Pouton and Seymour, Key issues in non-viral gene delivery, Adv Drug Deliv Rev. 46(1-3): 187-203, 2001.*
Read et al., Barriers to gene delivery using synthetic vectors, Adv Genet. 53: 19-46, 2005.*
Dobson, Gene therapy progress and prospects: magnetic nanoparticle-based gene delivery. Gene Ther. 13(4): 283-7, 2006.*
Tapia et al., The combination of DNA vectors expressing IL-12+IL-18 elicits high protective immune response against cutaneous leishmaniasis after priming with DNA-p36/LACK and the cytokines, followed by a booster with a vaccinia virus recombinant expressing p36/LACK. Microbes Infect. 5(2): 73-84, 2003.*
Doria-Rose et al., DNA vaccine strategies: candidates for immune modulation and immunization regimens, Methods, 31(3):207-16, 2003.*
Genbank accession No. Z83677, version Z83677.1 GI:1743284, submitted by Ortiz,G. et al. on Dec. 12, 1996 (3 pages).*
Grantham et al., Codon frequencies in 119 individual genes confirm consistent choices of degenerate bases according to genome type. Nucleic Acids Res. 8(9):1893-912, 1980.*
Ravindran, Progress in vaccine research and possible effector mechanisms in visceral leishmaniasis, Curr Mol Med. 4(6):697-709, 2004.*
Tabbara, Progress towards a Leishmania vaccine, Saudi Med J, 27(7):942-950, 2006.*
Molecular cloning, cell localization and binding affinity to DNA replication proteins of the p36/LACK protective antigen from Leishmania infantum, Gonzalez-Aseguinolaza et al., Eur. J. Biochem, 259, 909-916 (1999), Feb. 1999.
Rosenthal E, Marty P. Recent understanding in the treatment of visceral leishmaniasis, J. Postgrad Med 2003;49:61-8.
Induction of a Th1 Immune Response and Simultaneous Lack of Activation of a Th2 Response Are Required for Generation of Immunity to Leishmaniasis, Sjölander et al., The American Association of Immunologists, 0022-1767/98/$02.00.

(Continued)

Primary Examiner—Wu-Cheng Winston Shen
(74) Attorney, Agent, or Firm—Ursula B. Day

(57) ABSTRACT

Use of a combination of DNA expression constructs for the production of a remedy for the immunization against infections with leishmaniasis, as well as a corresponding vaccine. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

3 Claims, 2 Drawing Sheets

OTHER PUBLICATIONS

Vaccine requirements for sustained cellular immunity to an intracellular parasitic infection, Gurunathan et al., Nature Medicine, vol. 4, No. 12, Dec. 1998, pp. 1409-1415.

IL-12 is Required to Maintain a Th1 Response During Leishmania major Infection, Park et al., The American Association of Immunologists; 0022-1767/00/$02.00.

Designer Vaccines for Parasitic Diseases, F.E.G. Cox, International Journal for Parasitology, vol. 27, No. 10, pp. 1147-1157, 1997.

Hepburn NC, Cutaneous leishmaniasis: an overview. J Postgrad Med 2003; 49:50-4.

Immunoregulation of Cutaneous Leishmaniasis, Scott et al., J. Exp. Med, The Rockefeller University Press, 0022-1007/88/1675/10 $2.00.

Bacterial Lipoprotein-Based Vaccines Induce Tumor Necrosis Factor-Dependent Type 1 Protective Immunity against Leishmania major, Cote-Sierra et al., Infection and Immunity, Jan. 2002, p. 240-248, vol. 70, No. 1.

Gene gun-mediated delivery of an interleukin-12 expression plasmid protects against infections with the intracellular protozoan parasites Leishmania major and Trypanosoma cruzi in mice, Sakai et al., Immunology, 2000, 99, pp. 615-624.

Recombinant Vaccinia Viruses Expressing GP46/M-2 Protect against Leishmania Infection, McMahon-Pratt et al., Infection and Immunity, Aug. 1993, p. 3351-3359, vol. 61, No. 8.

Protective immune response against cutaneous leishmaniasis by prime/booster immunization regimens with vaccinia virus recombinants expressing Leishmania infantum p36/LACK and IL-12 in combination with purified p36, Gonzalo et al., Microbes and infection, 2001, pp. 701-711.

Vaccination with DNA Encoding the Immunodominant LACK Parasite Antigen Confers Protective Immunity to Mice Infected with Leishmania major, Gurunathan, et al., The Journal of Experimental Medicine, vol. 186, No. 7, Oct. 6, 1997, p. 1137-1147.

Vaccination with Plasmid DNA Encoding TSA/LmSTI1 Leishmanial Fusion Proteins Confers Protection against Leishmania major Infection in Susceptible BALB/c Mice, Campos-Neto et al., Infection and Immunity, Jun. 2002, p. 2828-2836.

The Potency and Durability of DNA- and Protein-Based Vaccines Against Leishmania major Evaluated Using Low-Dose, Intradermal Challenge, Méndez et al., The American Association of Immunologists, 0022-1767/01/$02.00, p. 5122-5128.

DNA vaccination with linear minimalistic (MIDGE) vectors confers protection against Leishmania major infection in mice, López-Fuertes et al., Vaccine 21 (2002) p. 247-257.

Attenuated Toxoplasma gondii ts-4 mutants engineered to express the Leishmania antigen KMP-11 elicit a specific immune response in BALB/c mice, Ramirez et al., Vaccine 20 (2002) p. 455-461.

Codon frequencies in 199 individual genes confirm consistent choices of degenerate bases according to genome type. Grantham et al., Nucleic Acids Research, vol. 8, No. 9, 1980, p. 1893.

Haem detoxification by an insect, Oliveira et al., Nature, vol. 400, Aug. 5, 1999, p. 517.

Optimization of DNA vaccination against cutaneous leishmaniasis, Mendez et al., Vaccine 20 (2002) 3702-3708.

Protection in dogs against visceral leishmaniasis caused by Leishmania infantum is achieved by immunization with a heterologous prime-boost regime using DNA and vaccinia recombinant vectors expressing LACK, Ramiro et al., Vaccine 21 (2003) 2474-2484.

Protective efficacy of a tandemly linked, multi-subunit recombinant leishmanial vaccine (Leish-111f) formulated in MPL adjuvant, Skeiky et al., Vaccine 20 (2020) 3292-3303.

* cited by examiner

AGENT FOR TREATING LEISHMANIA INFECTIONS

CONTINUING APPLICATION DATA

This application is a Continuation-In-Part application of International Patent Application No. PCT/DE2004/002383, filed on Oct. 22, 2004, which claims priority from European Patent Application No. 03090368.6, filed on Oct. 24, 2003. International Patent Application No. PCT/DE2004/002383 was pending as of the filing date of this application. The United States was an elected state in International Patent Application No. PCT/DE2004/002383.

BACKGROUND

1. Technical Field

This application concerns the use of a combination of DNA expression constructs for the production of a remedy for the immunization against infections with leishmaniasis, as well as a corresponding vaccine. The DNA expression constructs themselves are also an object of the embodiments described in the application.

2. Background Information

*Leishmania* are trypanosmatide flagellates of the order Kinetoplastida. They are passed on to different mammal species and humans by female blood-feeding sandflies of the species *Phlebotomus* and *Lutzomyia*. Leishmaniases are diseases with a diverse set of clinical appearances and constitute a major health problem. According to WHO estimates, about 12 million human beings are affected by the disease worldwide. About 2 to 9 percent of all HIV patients suffer from visceral leishmaniasis, making it the third most prevalent parasitic disease afflicting HIV patients. While serious tissue destructions occur with mucocutan and cutan leishmaniasis, an untreated visceral leishmaniasis (Kala-Azar), in most cases, has fatal results.

For the treatment of the disease, there are only a few clinically proved remedies available. Therefore chemotherapeutics—usually compounds of the heavy metal antimony—are used for the treatment of visceral leishmania for about 60 years. The substantially high toxicity of most of these preparations limits their use. Furthermore, *leishmania* has developed in many regions resistance against antimony preparations (J Postgrad Med. 2003 January-March; 49(1):61-8).

A therapy that is easy to get on and is protective is not yet existent.

Since persons who have survived infection develop a strong immunity against later infections, the development of an effective vaccination should be possible.

The vaccination or, respectively, the immune therapy of leishmaniasis, caused by intracellular parasites, should be possible by inducing a Th1-typical immune response. Within the state of art the importance of inducing a Th1-response in therapy or prevention of leishmaniases is stressed very often (Handman et al., J Immunol 160: 3949-57, Gurunathan et al., Nature Med: 4(12): 1409-15). As support for the induction of a Th1-typical immune response, the co-stimulatory cytokine IL-12 is referred to as being necessary adjuvant (Parker et al., J. Immunol. 140: 896-902).

Additionally, immune stimulatory nucleic acid sequences (ISS) can be used as adjuvant. The CpG-motifs of the ISS lead to an increase of the NK-cell and macrophage activity as well as to a strong stimulation of the cellular Th1 immune response. Covalently closed ISS with a length of 30 bp can preferably be used, as they are described for instance in EP 1 196 178 A1.

Different antigens were tested in various experimental vaccine protocols in mice. The immunological reaction to this infection in mice seems to be similar to that in humans, and probably also to that in dogs (Cox, Int. J. Parasitol. 263: 1147-1157). Antigens employed were gp63 (Scott et al., J. Exp Med. 168: 1675-1684), gp46 (McMahon-Pratt et al., Infection and Immunity 61: 3351-3359), p-4 and p-8 (Scott et al., Immunology 99: 615-624) and the antigen referred to as gp36 or LACK (Gonzales-Aseguinolaza et al., Eur. J. Biochem. 259: 909-916). The most successful vaccination protocol, primary immunization by p36 protein and secondary immunization by vaccinia virus encoding p36 and IL-12, led to an average decrease in lesions of 52% in comparison to non-vaccinated mice (Gonzalo et al., Microbes and Infection: 3 (9): 701-711).

Besides providing the 52% protection, vaccinia viruses have been used in the cited experiments as gene shuttles. Viral vectors represent the most commonly used gene shuttles because of their high transfection efficiency. However, the high risk of a cytotoxic reaction of the host caused by the transfected cells is known. Thus, the application of high doses of an adenovirus led in a clinical trial to the death of the patient; obviously the reason for this was a strong overreaction of the immune system (Lehrman, 1999, Nature 401: 517-518). Furthermore, the metamorphosis of an attenuated vaccination strain into a virulent strain can not be excluded because of its instability. Moreover viral parts themselves can act immunogenically, leading to a decrease of their efficiency by the patient's immune system.

In several experiments of the applicants, BALB/c mice have been immunized with expression constructs coding for the p36 LACK-antigen. Different vaccination protocols have been applied there. Within these studies, in one group a 57% protection against infections with *Leishmania major* could be obtained (L. Lopez-Fuertes et al., 2002, Vaccine 21: 247-257).

Gurunathan et al. used p36 LACK-antigen, coded by eukaryotic expression vectors, for vaccination experiments in mice (J. Exp. Med., Vol 186, No. 7, (1997): 1137-1147).

In other approaches, different antigen combinations have been used. With a mixture of plasmid DNA, coding for TSA and LmST11, the size of lesions could be minimized over a defined space of time (A. Campos-Neto et al., 2002, Infection and Immunity: 2828-2836). The triple combination of the antigens LACK, LmST11 and TSA could inhibit mostly the appearance of dermal lesions after infection and resulted in protection for several weeks (S. Mendez et al., 2001, J. of Immunology 166: 5122-5128).

All cited experiments have in common that only protection in part—and thus an insufficient protection—against infections with leishmaniasis was possible. Moreover, a big drawback is that the vaccination combinations have not been tested in dogs, the main transmitter, but rather only in mice. A further disadvantage is that plasmids were used as gene shuttles. Plasmids are gained by bacterial fermentation, by which they typically contain, besides the wanted gene DNA necessary for replication and selection, genes that are resistant against the antibiotics used during fermentation. The use of gene expression constructs based on plasmid DNA has the inherent risk of spreading antibiotic resistant genes, which is especially not justifiable at vaccination campaigns. The described disadvantages of plasmid based expression vectors have resulted in massive opposition to their use within clinical practice.

OBJECT OR OBJECTS

Coming from this state of the art, it is an objective of at least one embodiment disclosed in this application to provide one or more DNA expression constructs that can be used for producing a remedy for the efficient immunization against leishmaniasis.

SUMMARY

The objective is solved by the features of the embodiments disclosed herein.

As DNA expression constructs, according to at least one embodiment, preferably minimalistic, immunological defined gene expression constructs are used, referred to as MIDGE in the following (MIDGE®: MINIMALISTIC IMMUNOLOGICALLY DEFINED GENE EXPRESSION VECTORS, see EP 0 941 318 B1, U.S. Pat. No. 6,451,593 B1). The MIDGE-vectors have the advantage, that they do not need structures that are not essential for the therapeutic efficiency. The MIDGE-vector is commercially available from the company Mologen AG, located at Fabeckstrasse 30, Berlin, Germany.

According to at least one embodiment, it is preferably intended that, for the generation of an immune response, the immunogenic antigen p36 LACK be used in combination with *Leishmania infantum* thiol-specific antioxidant protein antigen (TSA), the *Leishmania infantum* kinetoplastid membrane protein 11 antigen (Kmp-11), and the *Leishmania infantum* glycoprotein 63 (gp63) antigen.

Hence the use of a DNA expression construct for the production of a remedy for the immunization against leishmaniasis infections is intended, where said DNA expression construct contains one or more coding nucleic acid sequences, leading to the expression of the *Leishmania infantum* antigen thiol-specific antioxidant protein Gene (TSA), glycoprotein gp63 and kinetoplastid membrane protein 11 (Kmp-11) or alleles or derivates thereof with corresponding function.

It is also preferable to use two or three DNA expression constructs for the production of a remedy for immunization against leishmaniasis infections, where each of the DNA expression constructs contain one or more coding nucleic acid sequences that collectively lead to the expression of the *Leishmania infantum* antigens thiol-specific antioxidant protein Gen (TSA), glycoprotein gp63, and kinetoplastid membrane protein 11 (Kmp-11), or alleles or derivates thereof with corresponding function.

According to at least one embodiment, it is intended that at least two *Leishmania infantum* antigens are expressed as fusion proteins. This can be on one hand the fusion protein—as expression product—of thiol-specific antioxidant protein Gene (TSA) and kinetoplastid membrane protein 11 Gene (Kmp-11), or a combination thereof. Consequently with respect to the three different *Leishmania infantum* antigens a fusion protein—as expression product—of thiol-specific antioxidant protein Gen e(TSA), glycoprotein gp63 gene and kinetoplastid membrane protein 11 Gene (Kmp-11), or a combination thereof, is preferred.

The phrase "combination thereof" means every order/alignment of the genes, respectively their reading order, for instance [TSA-Kmp-11] or [Kmp-11-TSA], and also [TSA-gp63-Kmp-11] or (TSA-Kmp-11-gp63] or [Kmp-11-TSA-gp63] etc.

Thus a gene expression construct coding for different fusion proteins is also intended. The fusion protein consists of a combination of at least two of the mentioned antigens (TSA, Kmp-11). The bi-fusion protein is used alone or in combination with the antigen gp63.

Yet the fusion protein can consist of three antigens as described. This concerns a combination of the antigens TSA, Kmp-11 and gp63.

Further, a use is preferred where, in addition to the described DNA expression constructs, regardless if fusion proteins will be expressed or not, a DNA expression construct for expression of the *Leishmania* antigen p36 LACK or a allele or derivate thereof with corresponding function is contained. Thus the p36 LACK antigen can be optionally added to this cocktail.

The designation "allele or derivate thereof with corresponding function" means, in connection with at least one of the embodiments disclosed herein, homologue sequences where the degree of homology is unremarkable, in so far as the same function of the gene is guaranteed and kept.

As a gene shuttle a linear double stranded covalently closed MIDGE expression cassette is used. The immunogenic polynucleotide sequences are present as expression constructs, consisting of covalently closed linear deoxyribonucleotide molecules having a linear double stranded region, where the double-strand-forming single strands are linked by short single stranded loops of deoxyribonucleic acid nucleotides, and where the double-strand-forming single strands consist only of a coding sequence under control of a promoter sequence operable in the animal that is to be vaccinated and a terminator sequence. Thus, the expression cassette essentially consists only of the coding region, the promoter, and, if necessary, a termination sequence, so that the construct contains essentially only information necessary for the expression of the wanted gene, avoiding the drawbacks of gene shuttles with viral origin. Further, according to at least one embodiment, it is intended that the expression construct or constructs are linked to an oligopeptide of 3 to 30 amino acids, where the oligopeptide consists half of basic amino acids selected from the groups' arginine and lysine for an increase of transfection efficiency. A nuclear localization sequence is especially preferred, particularly the nuclear localization sequence d (NLS) representing peptide sequence PKKKRKV (proline-lysine-lysine-lysine-arginine-lysine-valine) from Simian Virus SV-40. In particular for the SV-40-NLS it has been demonstrated that proteins up to 465 kDa are directed to the cell nucleus (Lanford et al. 1986, Cell 15; 46 (4): 575-82). This capability of the peptide has been used by its coupling to DNA for an improvement of gene transfer.

or the eleven amino acid comprising T-peptide fragment YGRKKRRQRRR of HIV-1 gene product TAT.

Thus proteins that amplify the transfection efficiency of DNA vaccines, for instance cationic peptides and proteins, are preferred as parts of expression constructs.

The coding polynucleotide sequences can also be circular double stranded expression vectors.

It is known that an optimized codon usage (Codon Usage Optimization) within the expression construct, especially for codons used in mammals, leads to a strong increase of protein expression (Grantham et al., Nucleic Acids Res 1980, 9:1893-912). To express more antigen in-vivo and to receive by this a stronger immune response, which results in an efficient and enduring protection against infections with leishmaniasis, the wild type sequence of gp63 has been optimized. Optimizing means the codon adaptation, also designated as "Codon-Usage-Optimization". For that purpose, a cloning strategy was developed that allows the synthesis of the optimized DNA sequence of gp63 from oligonucleotides.

According to at least one embodiment, the sequence of the *Leishmania infantum* gp63 antigen was codon optimized (Seq. ID 5). A DNA expression construct comprising this sequence is therefore also preferred.

DNA expression constructs according to at least one embodiment provide a basis for producing a vaccine for the treatment of leishmaniasis infection diseases and are part of a corresponding vaccine.

In another preferred embodiment, the vaccine can contain immunogenic stimulatory nucleic acid sequences (ISS). The immunogenic stimulatory nucleic acid sequences, containing CpG-motifs, comprise a circular strand of deoxyribonucleic acid with a partially complementary, anti-parallel base sequence. In an especially preferred embodiment, the immunogenic stimulatory nucleic acid sequences are dumbbell-shaped.

Likewise, the combination of vaccines disclosed herein with transfection-increasing compounds, such as PEI (polyethyleneimine), is possible.

For transfection, biological, chemical and/or physical methods can be used which belong to the state of art, such as, for instance, transfection by ballistic transfer or electroporation. In a preferred embodiment, the transfection can be carried out by transfection by intradermal injection with a syringe or needle-free injection equipment.

The added sequence protocol, being part of the application and the present description, lists the sequences.

Seq. ID Sequence Name/Description

Seq. ID 1 DNA sequence of *Leishmania infantum* kinetoplastid membrane protein 11 Gene (Kmp-11)

Seq. ID 2 Protein sequence of *Leishmania infantum* kinetoplastid membrane protein 11 antigen (Kmp-11)

Seq. ID 3 DNA sequence of *Leishmania infantum* thiol-specific antioxidant protein Gen (TSA)

Seq. ID 4 Protein sequence of *Leishmania infantum* thiol-specific antioxidant protein antigen (TSA)

Seq. ID 5 DNA sequence of codon optimized *Leishmania infantum* antigen glycoprotein 63 (gp63)

Seq. ID 6 Protein sequence of codon optimized *Leishmania infantum* antigens glycoprotein 63 (gp63)

Seq. ID 7 DNA sequence of *Leishmania infantum* antigen p36 (LACK)

Seq. ID 8 Protein sequence of *Leishmania infantum* antigen p36 (LACK)

Seq. ID 9 Nuclear localization sequence (peptide sequence) of SV40

Seq. ID 10 Large T-peptide fragment of HIV-1 gene product TAT (TAT-peptide)

Seq. ID 11 to

Seq. ID 36 synthetic DNA oligomeres as described below.

Further advantageous measures are described herein below. At least one of the embodiments will be described and discussed in the following by figures and examples.

DESCRIPTION OF EMBODIMENT OR EMBODIMENTS

The surprising effect of the combination of DNA expression constructs and a remedy according to at least one embodiment containing such a combination becomes apparent by the representations and figures. Thereby means:

MIDGE-NLS p36 with NLS coupled MIDGE coding for p36 LACK antigen

MIDGE-NLS TSA with NLS coupled MIDGE coding for TSA antigen

MIDGE-NLS gp63 with NLS coupled MIDGE coding for gp63 antigen

Figure 1:
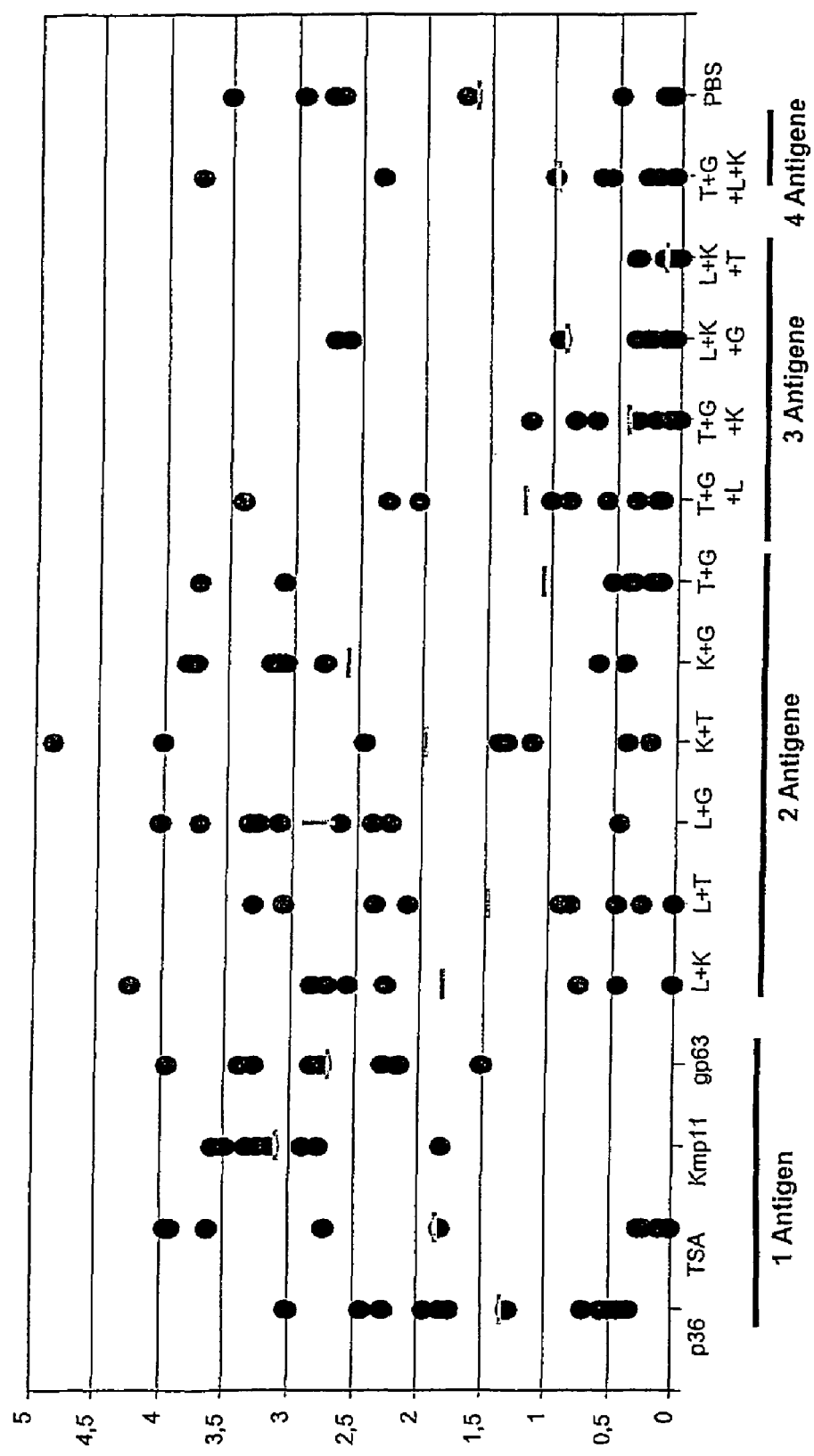
FIG. 1 shows a chart relating to the development of lesions within 8 weeks after challenge infection in mice.

MIDGE-NLS Kmp-11 with NLS coupled MIDGE coding for Kmp-11 antigen pMCVp36 Plasmid coding for p36 LACK antigen pMCV TSA Plasmid coding for TSA antigen pMCV gp63 Plasmid coding for gp63 antigen pMCV Kmp-11 Plasmid coding for Kmp-11 antigen FIG. 1: The development of lesions within 8 weeks after challenge infection in mice.

Caption:
L+K: LACK in combination with Kmp-11
L+T: LACK in combination with TSA
L+G: LACK in combination with gp63
K+T: Kmp-11 in combination with TSA
K+G: Kmp-11 in combination with gp63
T+G: TSA in combination with gp63
T+G+L: TSA in combination with gp63 and LACK
T+G+K: TSA in combination with gp63 and Kmp-11
L+K+G: LACK in combination with Kmp-11 and gp63
L+K+T: LACK in combination with Kmp-11 and TSA
T+G+L+K: TSA in combination with gp63, LACK and Kmp-11
PBS: Control group: PBS FIG. 1 shows different combinations of the used antigens in mice. The antigens were used alone, in six different double combinations, in four different triple combinations, and in one quadruple combination. As a relevant parameter for a clinical success of the vaccination, the growth of the lesions caused by infection was determined. The increase of growth of the lesions is plotted on the ordinate in millimeters. The different antigen combinations are plotted as abscissa. It is obvious that within the group of double combinations the combination of TSA and gp63 gives best vaccination protection. The second best protection is reached by the combination LACK and TSA. Within the group of triple combinations, the group LACK, Kmp-11 and TSA gives best protection. The achieved vaccination success results in a clearly minimized size of the present lesions. The second best vaccination protection is achieved by the combination of the antigens TSA, gp63, and Kmp-11. Within this group a medium lesion size of 0.5 millimeters is obtained. The value of 0.5 millimeters represents a threshold for the human eye to recognize and analyze lesions. This means that animals treated with the combination of TSA, gp63, and Kmp-11, per that definition, show no lesions, i.e. the assessed lesions are below the detection limit. In comparison to this, the untreated mice of the control group have a medium average lesion size of 1.7 millimeters. As well these animals showed a strong swelling and redness of the paws, symptoms that could not be observed in the protected groups representing clear signs of inflammation caused by infection.

Figure 2:
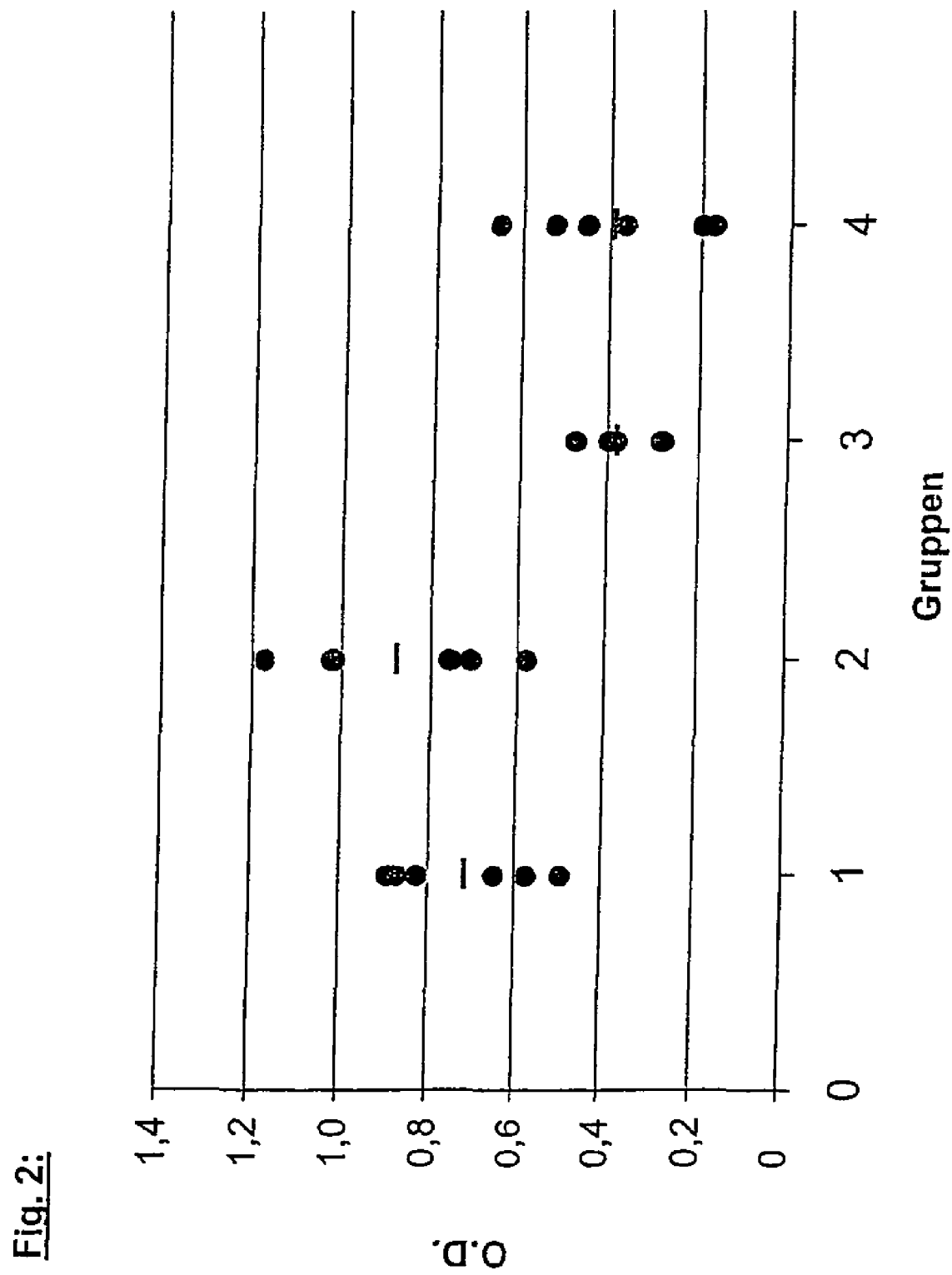
FIG. 2 shows a chart relating to the determination of total IgG titer in dogs before challenge infection with *Leishmania infantum* promastigotes.

FIG. 2: The determination of total IgG titer in dogs before challenge infection with *Leishmania infantum* promastigotes.

Caption:
    Group 1: MIDGE-NLSp36 LACK
    Group 2: MIDGE-NLS 4 antigen combination
    Group 3: Plasmid 4 antigen combination
    Group 4: Control group: PBS The dots represent data from single dogs, as the horizontal bars mark the average value of the corresponding group. The optical density (OD) increases with the concentration of serum antibodies. In FIG. 2, a clear difference is obvious between the concentration of anti-*Leishmania* antibodies of groups 1 and 2 on one hand, and the groups 3 and 4 on the other hand. The dogs of group 1, vaccinated with MIDGE-NLS-LACK, and the dogs of group 2, which received the combination of four antigen sequences in MIDGE-NLS, possessed more antibodies against *Leishmania infantum* as compared to the dogs of groups 3 and 4. It is remarkable that no antibodies were detectable in group 3, although the same antibodies sequences as in group 2 were used. This demonstrates that the combination of the four antigen sequences, especially in combination with MIDGE-NLS vectors, is appropriate for induction of a humoral immune response. Also in comparison to group 1, the dogs of group 2 had on average more antibodies. This leads to the conclusion that the combination of the four antigens is advantageous in comparison to the sole application of LACK. In the following the results of the experiments are discussed in more detail.

In a vaccination experiment in mice, the effectiveness of different combinations of the antigens to reach a maximal protection against infections with leishmaniasis was tested. As a parameter for induced protection the suppression of lesion growth by the used vaccine combination was taken. For evaluation of the protection efficiency, a challenge infection with *Leishmania infantum* promastigotes was performed. The evaluation of the lesion growth was done weekly. The results depicted in FIG. 1 are taken from week eight after the challenge infection. Basically all animals vaccinated with one antigen or a double combination of the antigens developed earlier lesions than animals vaccinated with a triple or quadruple combination. A good vaccination result was achieved with a triple combination of the antigens Kmp-11, TSA and p36 LACK. A comparable protection was attained with the antigen combination TSA, gp63 and Kmp-11. The surprising success gets obvious by the fact that the size of lesions for both triple combinations (TSA, gp63, Kmp-11 und p36 LACK, Kmp-11, gp63) was below the threshold of 0.5 millimeters, meaning that no apparent lesions developed. Thus the size of lesions of the vaccinated animals is 100% less than that of the unvaccinated control group.

TABLE 1

Composition of antigen combinations for a vaccination experiment in mice.

| | Group | Number of animals | Amount of DNA [microgram] |
|---|---|---|---|
| 1. | MIDGE-NLS-p36 LACK + Kmp-11 | 9 | 50 |
| 2. | MIDGE-NLS-p36 LACK + TSA | 9 | 50 |
| 3. | MIDGE-NLS-p36 LACK + gp63 | 9 | 50 |
| 4. | MIDGE-NLS-Kmp11 + TSA | 9 | 50 |
| 5. | MIDGE-NLS-Kmp11 + gp63 | 9 | 50 |
| 6. | MIDGE-NLS-TSA + gp63 | 9 | 50 |
| 7. | MIDGE-NLS-TSA + gp63 + p36 LACK | 9 | 50 |
| 8. | MIDGE-NLS-TSA + gp63 + p36 LACK + Kmp-11 | 9 | 50 |
| 9. | MIDGE-NLS-p36 LACK | 9 | 50 |
| 10. | MIDGE-NLS-TSA | 9 | 50 |
| 11. | MIDGE-NLS-Kmp-11 | 9 | 50 |
| 12. | MIDGE-NLS-gp63 | 9 | 50 |
| 13. | MIDGE-NLS-TSA + gp63 + Kmp-11 | 9 | 50 |
| 14. | MIDGE-NLS-p36 LACK + Kmp-11 + gp63 | 9 | 50 |
| 15. | MIDGE-NLS-p36 LACK + Kmp-11 + TSA | 9 | 50 |
| 17. | PBS | 9 | 50 |

Per group nine female BALB/c mice were tested. The animals were vaccinated with 50 micrograms of DNA. For the antigen combinations, 50 micrograms of each antigen were used. After two weeks the second vaccination was done (boost). Three weeks after the boost, the challenge infection was carried out with $5 \times 10^4$ *Leishmania infantum* promastigotes, resting in the stationary meta-cyclic phase. They were injected in the right back paw. The state of injections was checked weekly. The size of lesions was determined with an electronic slide gauge and by comparison with the untreated left back paw. Also, in a following experiment in 4- to 12-month-old female beagle dogs, different vaccine combinations were used, but differing in the used combination of antigens. Group 1 received only one antigen, namely p36 LACK antigen. This antigen gave in earlier experiments good protection and should be proved in dogs (L. Lopez-Fuertes et al., 2002, Vaccine 21: 247-257). Group 3 received different plasmids encoding for the *Leishmania infantum* antigens TSA, Kmp-11, gp63 und p36 LACK. This group was used for comparison of vectors and efficiency with group 2, consisting of the same antigen combinations, but containing peptide coupled MIDGE vectors.

Four vaccination groups with six animals each were built, which animals, in a 15 days period, were each vaccinated intradermally four times with 200 microgram DNA per construct (see table 3). Before starting the experiment and after each immunization of the animals, blood was taken for serological examination besides typical veterinary checks.

To determine which kind of immune response was induced by the infection, different methods were used. To the type of methods allowing conclusions about the kind of immune response belongs the so-called "Delayed Type Hypersensitivity"-test (DTH-test). By measuring the thickness of the dermis at the injection position 72 hours after antigen application, it is possible to determine relatively correctly if a delayed hypersensitive response, and thus a specific T-cell reaction to the antigen, was induced. The results are summarized in the following table:

TABLE 2

| Group | Dogs | DTH-test before vaccination | DTH-test after vaccination |
|---|---|---|---|
| MIDGE-NLSp36 LACK | 1 | − | + |
| | 2 | − | − |
| | 3 | − | − |
| | 4 | − | + |
| | 5 | − | − |
| | 6 | − | − |

TABLE 2-continued

| Group | Dogs | DTH-test before vaccination | DTH-test after vaccination |
|---|---|---|---|
| MIDGE-NLS | 1 | − | + |
| TSA, p36, Kmp11, gp36 | 2 | − | + |
| | 3 | − | + (?) |
| | 4 | − | − |
| | 5 | − | + |
| | 6 | − | + |
| Plasmid | 1 | − | + |
| TSA, p36 LACK, Kmp11, gp36 | 2 | − | + |
| | 3 | − | − |
| | 4 | − | ++ |
| | 5 | − | − |
| | 6 | − | + |
| PBS Buffer | 1 | − | − |
| | 2 | + | − |
| | 3 | − | + |
| | 4 | − | + (?) |
| | 5 | − | − (?) |
| | 6 | − | − |

Table 2 shows the results of a "Delayed Type Hypersensitivity"-test (DTH-test). A local swelling of the dermis is assessed as a positive DTH-test (marked in the figure with "+" or "++") and indicates that the corresponding animal developed antigen specific T-cell memory cells caused by infection, and thus a cellular immune response took place. As described above, the cellular immune response is crucial for prophylaxis and therapy of leishmaniasis diseases. Before starting the experiment, a DTH-test was performed, to insure that no animal had already developed a cellular immune response against *Leishmania infantum* because of an earlier infection/vaccination. All animals, except one, reacted negatively in the DTH-test and by this fulfilled the prerequisite for the experiment. A positive reaction after finishing the immunization means that the immunization caused a specific cellular immune response against *Leishmania infantum*. This is a vaccination success and justifies expectations for better protection against infections.

After the last vaccination the DTH-test was repeated. One expected that nearly all animals were positive. Because the previously positive tested animal was now negative, one can assume that this is also true for the first DTH-test which had to be misinterpreted.

The immune response caused by vaccination was additionally characterized by serological examinations. FIG. 2 summarizes the results of the ELISA test of specific antigens against *Leishmania infantum* within the serum of the immunized dogs. Generally the antibody concentrations in the sera of the tested dogs were not very high. This result is in accordance with the expectations, because the aim of immunization was a cellular immune response and not a humoral immune response.

TABLE 3

Composition of vaccination groups for an experiment against Leishmania infantum in dogs.

| Group | Used antigen | Number of Animals | Amount of DNA | Applied Volume |
|---|---|---|---|---|
| 1 | MIDGE-NLS-p36 LACK | 6 | 200 μg per construct | 500 μl per animal |
| 2 | MIDGE-NLS-TSA, MIDGE-NLS-Kmp-11, MIDGE-NLS-gp63, MIDGE-NLS-p36 LACK | 6 | 200 μg per construct | 500 μl per animal |
| 3 | pMCV-TSA, pMCV-KMP-11, pMCV-gp63, pMCV-p36 LACKMIDGE | 6 | 200 μg | 500 μl per animal |
| 4 | PBS buffer | 6 | — | 500 μl per animal |

The success of immunization can be described by a challenge reaction of the animal to the germ. Four weeks after the last immunization an intravenously applied challenge infection with $5 \times 10^7$ *Leishmania infantum* promastigotes was carried out. The degree of infection and thus the protection received by immunization is determined by clinical pathological examinations, including the examination of swelling of the lymph nodes, loss of weight, degeneration with corresponding change of muscle color, over increasing growth of nails, and lesions of the dermis as well as changes in the hemogram. The presence and the quantity of the germ are determined by PCR. A comparison of the groups after 11 months after challenge infection, with reference to the clinical symptoms, shows the results as described in the following paragraph.

A clear difference between group 2 and the control group is visible. In group 2, only one dog suffered from leishmaniasis, as in the control group four of six dogs got leishmaniasis. In group 1, the number of infected dogs was also smaller than in the control group, as group 3 showed only a slight difference to the control group. A direct comparison of the effect of MIDGE-NLS with plasmids coding for exactly the same antigen (group 2 and group 3) shows that MIDGE-NLS gives better protection against leishmaniasis, as it was possible with plasmid. The results of the experiments allow the conclusion that it is possible to inhibit the development of clinical symptoms of leishmaniasis in dogs by immunization with a combination of the four MIDGE-NLS coding antigens. A comparable result, as achieved with a vaccine according to at least one embodiment containing MIDGE-NLS coding for the four antigens, is to the knowledge of the applicant only described by Ramiro et al., (Vaccine 3696, 2003: 1-11). However, in contrast to MIDGE-NLS, Ramiro et al. used in their study a recombinant Vaccinia Virus (rVV) as the boost vaccine. Recombinant Vaccinia Viruses are genetically modified viruses that represent a commonly known high security risk (Lehrman, 1999, Nature 401: 517-518).

Example 1

Cloning of Plasmid pMCVp36

Starting from the plasmid pSCp36 two fragments were amplified by PCR:

```
1. PCR ca. 800 bp;
Primer left:
5'-TTATATGGTACCATGAACATACGAGGGTCACCT
Primer right:
5'-TTATATGAGCTCAGAAGACACGGACAGGGACCTCTTCCGTCG
```

```
2. PCR ca. 950 bp;
Primer left:
5'-TTATATGGTACCATGAACATACGAGGGTCACCT
Primer right:
5'-TTATATGAGCTCTTACTCGGCCGTCGGAGATGG
```

The PCR product derived from the second PCR reaction was digested with Eco31I and the smaller fragment (approx. 200 bp) was isolated.

The PCR product from the first PCR reaction was digested with BpiI.

The 200 bp fragment and the digested fragment from the first PCR reaction were ligated and subsequently digested with KpnI and SacI, and inserted by ligation into the pMOK vector that had been digested by KpnI and SacI. The resulting plasmid was named pMCVp36.

Example 2

Cloning of Plasmid pMCVKmp-11

The gene was amplified by PCR from cDNA of *Leishmania infantum*. The PCR product was cloned into pMCV1.4 and sequenced after digestion with KpnI and XhoI. The resulting plasmid was named pMCVKpm11.

```
Primer left:
5'-ATTATAGGTACCATGGCCACCACGTACGAG

Primer right:
5'-TTAATTCTCGAGTTACTTGGATGGGTACTGCG
```

Example 3

Cloning of Plasmid pMCVTSA

The gene was amplified by PCR from cDNA of *Leishmania infantum* and one base substituted without changing the amino acid sequence deleting an Eco31I cleavage site. The final PCR product was digested with KpnI and XhoI and cloned into the vector pMCV1.4 followed by sequencing. The resulting plasmid was named pMCVTSA.

```
left Primer:
5'-AATTATGGTACCATGTCCTGCGGTAACGCCAAGATC right Primer:
5'-AATATACTCGAGTTACTGCTTGCTGAAGTATCCTTCGAC left mutation primer:
5'-TACCGCGGTCTCTTCATCATCG right mutation primer:
5'-ATTGGGGGTCTCGATGAATAGACCGCGGTAGG
```

Example 4

Cloning Strategy for Codon-Usage Optimization of gp63

The oligonucleotides with a length of 18 to 28 base pairs were ordered (MWG Biotech). Two oligonucleotides with a length of 90 bases, representing a forward and a backwards strand, were annealed and ligated. The annealed oligonecleotides had on both ends a four base overhang. Attention was paid to the fact that the overhangs could be found only once and were not palindromes. The oligonecleotides (forward and backward strand) were annealed by heating to 80° C. in kinase buffer and subsequent slow cooling to room temperature. Afterwards ATP and polynukleotidkinase (PNK) added and the oligonecleotides were phosphorylated for one hour. In the next step neighboring oligonucleotides were mixed and ligated (oligonucleotide 1+2, oligonucleotide 3+4). After one hour an aliquot of the ligation of oligonucleotide 1+2 and oligonucleotide 3+4 were mixed. This procedure was repeated up to a length of the ligation product of about 300 bp. An aliquot of each final ligation step was used as template for a PCR with the flanking primers. The PCR product was cloned into the TOPO-TA-Cloning vector (Invitrogen) and sequenced. This was done in total with six fragments of the whole gene. The six single fragments were cleaved from the intermediate plasmid with Eco31I and ligated. The ligation product with correct size was amplified in a final PCR, digested with KpnI and SacI, gel extracted and cloned into the vector pMCV1.4, digested with the same enzymes. Afterwards the sequence was checked by sequencing. The resulting plasmid was named pMCVgp63.

Primer for the 6 assembled fragments:

```
Fragment 1:
left primer:
ATTATTGGTACCATGTCTGTGGACT
right primer:
TTATATGGTCTCTCTCAGGGCTCCCCAGTTG Fragment 2:
left primer:
ATTATAGGTCTCCTGAGAATTGCTGTGTCCACAGAG
right primer:
TTATATGGTCTCACAGAGGCCACATACATCACAA Fragment 3:
left primer:
TATTATGGTCTCCTCTGTGCCCTCTGAGGAGGGAGTGCTGGCC
right primer:
AATTATGGTCTCCTCAATCTCCAGGTACTCCAGG Fragment 4:
left primer:
ATTATAGGTCTCATTGAGGACCAGGGAGGAG
right primer:
TAATATGGTCTCGTGTCTGGTCACTCCACACTTG Fragment 5:
left primer:
ATTATAGGTCTCAGACACCCAGACCTGCCCC
right primer:
TTATATGGTCTCGGGGTGCAGTTGGCATAGCC Fragment 6:
left primer:
ATATATGGTCTCCACCCCAGGCCTGAGAGTGG
right primer:
TAATATGAGCTCCTACAGGGCCACAGCCAGCAGG Whole sequence:
left primer:
ATTATTGGTACCATGTCTGTGGACT
right primer:
TAATATGAGCTCCTACAGGGCCACAGCCAGCAGG
```

Example 5

Coupling of NLS to Oligonucleotides

Attachment of NLS was done as follows: the NLS peptide comprising the sequence PKKKRKV was coupled to the ODN in two steps. First, the modified oligonucleotide 5'-PH-dGGG AGT CCA GT xT TTC TGG AC (where xT represents an amino-modified thymine base with a C2 amino linking residue; =ODN 1) was activated by sulfo-KMUS (5 mM) in PBS at room temperature. The reaction was stopped after 120 min by adding 50 mM tris(hydroxymethyl)-aminomethane, and the activated ODN was obtained after ethanol precipitation (300 mM NaOAc pH 5.2, 5.5 mM MgCl2, 70% ethanol), centrifugation and a single round of washing with 70% ethanol. The ODN thus obtained was dissolved in PBS at 0.1 mM and reacted with the activated peptide (0.2 mM) for one hour at room temperature. The reaction was controlled by gel electrophoresis and ethidium bromide staining. The resultant NLS-attached ODN was purified by HPLC and used for the synthesis of MIDGE-NLS constructs.

Example 6

Production of MIDGE-NLSp36

MIDGE are linear covalently closed expression cassettes that only consist of the CMV promoter, an intron, the respective gene sequence and a polyadenylation sequence (see EP 0 941 318 B1). The constructs were obtained as follows: the plasmid pMCVp36 as described in example 1.1 was digested completely with Eco31I. Ligation with 5' phosphorylated hairpin-shaped 5'-PH-GGG AGT CCA GT XT TTC TGG AC (=ODN 1) and 5'-AGG GGT CCA GTT TTC TGG AC-3' (=ODN 2), was achieved using T4 DNA ligase in the presence of Eco31I, and stopped by heating to 70° C. The resulting mix was concentrated and treated with Eco31I and T7 DNA polymerase in the absence of deoxyribonucleotide triphosphates. Purification was performed by anion exchange chromatography.

The production of MIDGE-NLS-TSA, Kmp-11 and gp63 was done in analogy.

Example 7

DTH-Test (Delayed Type Hypersensitivity-Test)

During this test a minimal amount of antigen is applied to the upper dermal stratum of the test animal. The thickness of the dermis at the position of injection was determined exactly before. Afterwards one observes if the dermis at the position of injection alters inflammable. A characteristic for an immune response to the antigen caused by sensitized T-cells is an inflammation that is detectable after 48 to 72 hours. The clinical symptoms like local dermal swelling, redness and eventually pain, can be traced back to the effect of cytokines. A local dermal swelling is evaluated as positive DTH-test (see table 1 marked with "+" or "++") and indicates that the specific animal has developed antigen specific T-memory-cells caused by infection.

Example 8

Determination of Total Antibodies after Immunization

In FIG. 2 are the results of the ELISA detection of specific antibodies against *Leishmania infantum* within the serum of immunized dogs depicted. Before challenge infection sera of all dogs were taken. The determination of total IgG antibody titer was performed by ELISA, where the absorption is determined in OD (optical density) at a wavelength of $\lambda$=406 nm.

The components disclosed in the various publications, disclosed or incorporated by reference herein, may possibly be used in possible embodiments, as well as equivalents thereof.

This application relates to the use of a combination of DNA expression constructs for the production of a remedy for the immunization against infections with leishmaniasis, as well as a corresponding vaccine. The DNA expression constructs it selves are also an objective of at least one embodiment. According to at least one embodiment it is preferably intended, that the immunogenic antigen p36 LACK is used in combination with *Leishmania infantum* thiol-specific antioxidant protein antigen (TSA), the *Leishmania infantum* kinetoplastid membrane protein 11 antigen (Kmp-11) and the *Leishmania infantum* glycoprotein 63 (gp63) antigen for the generation of an immune response. As DNA expression constructs plasmids can be used, preferably minimalistic, immunological defined gene expression constructs (MIDGE) are used according to at least one embodiment. Further the DNA expression constructs according to at least one embodiment are used for the production of a vaccine of leishmaniasis infection diseases and are part of a corresponding vaccine.

One feature or aspect of an embodiment is believed at the time of the filing of this patent application to possibly reside broadly in a method for using a DNA expression construct for the production of a remedy for immunization against leishmaniasis infections, whereas said DNA construct contains one or more coding nucleic acid sequences, that lead to the expression of the *Leishmania infantum* antigens thiol-specific antioxidant protein Gene (TSA), glycoprotein gp63 and kinetoplastid membrane protein 11 (Kmp-11) or alleles or derivates thereof with corresponding function.

Another feature or aspect of an embodiment is believed at the time of the filing of this patent application to possibly reside broadly in a method for using two or three DNA expression constructs for the production of a remedy for immunization against leishmaniasis infections, whereas said DNA expression constructs contain each one or more coding nucleic acid sequences, that lead collectively to the expression of the *Leishmania infantum* antigens thiol-specific antioxidant protein Gen (TSA), glycoprotein gp63 and kinetoplastid membrane protein 11 (Kmp-11) or alleles or derivates thereof with corresponding function.

Yet another feature or aspect of an embodiment is believed at the time of the filing of this patent application to possibly reside broadly in a method where at least two *Leishmania infantum* antigens are expressed as fusion proteins.

Still another feature or aspect of an embodiment is believed at the time of the filing of this patent application to possibly reside broadly in a method where the fusion protein is the expression product of thiol-specific antioxidant protein Gene (TSA) and kinetoplastid membrane protein 11 Gene (Kmp-11), or a combination thereof.

A further feature or aspect of an embodiment is believed at the time of the filing of this patent application to possibly reside broadly in a method where the fusion protein is the expression product of thiol-specific antioxidant protein Gene (TSA), glycoprotein gp63 Gene and kinetoplastid membrane protein 11 Gene (Kmp-11) or a combination thereof.

Another feature or aspect of an embodiment is believed at the time of the filing of this patent application to possibly reside broadly in a method where additionally a DNA expression construct for the expression of the leishmaniasis antigen p36 LACK or a allele or derivate thereof with corresponding function is contained.

Yet another feature or aspect of an embodiment is believed at the time of the filing of this patent application to possibly reside broadly in a method where the coding polynucleotide sequences are expression constructs consisting of covalently closed linear deoxyribonucleic acid molecules, having a linear double stranded region, where the double stranded forming single strands are linked by short single stranded loops of deoxyribonucleic acid nucleotides, where the double strand forming single strands consist only of a coding sequence under control of a promoter sequence operable in the animal that is to be vaccinated and a terminator sequence.

Still another feature or aspect of an embodiment is believed at the time of the filing of this patent application to possibly reside broadly in a method where the coding polynucleotide sequences are present as circular double stranded expression vectors.

A further feature or aspect of an embodiment is believed at the time of the filing of this patent application to possibly reside broadly in a method where the DNA expression construct is covalently linked to one or more oligopeptides to increase transfection efficiency.

Another feature or aspect of an embodiment is believed at the time of the filing of this patent application to possibly reside broadly in a method where each DNA expression construct is linked to an oligopeptide of 3 to 30 amino acids, where the oligopeptide consists half of basic amino acids selected from the groups arginine and lysine.

Yet another feature or aspect of an embodiment is believed at the time of the filing of this patent application to possibly reside broadly in a method where the linked oligopeptides have the amino acid sequence YGRKKRRQRRR.

Still another feature or aspect of an embodiment is believed at the time of the filing of this patent application to possibly reside broadly in a method where the linear covalently closed DNA expression constructs are modified with a peptide containing the nuclear localization sequence (NLS) of large T-antigen from SV40 PKKKRKV.

A further feature or aspect of an embodiment is believed at the time of the filing of this patent application to possibly reside broadly in a method for using the DNA expression constructs according to at least one of the previous claims for the production of a vaccine for the treatment of leishmaniasis infection diseases.

Another feature or aspect of an embodiment is believed at the time of the filing of this patent application to possibly reside broadly in a vaccine for the treatment of leishmaniasis infection diseases, containing a remedy as described herein.

Yet another feature or aspect of an embodiment is believed at the time of the filing of this patent application to possibly reside broadly in a vaccine which contains additionally adjuvants and/or immunogenic stimulatory nucleic acid sequences with one or more CpG-motifs.

Still another feature or aspect of an embodiment is believed at the time of the filing of this patent application to possibly reside broadly in a vaccine where the immunogenic stimulatory nucleic acid sequences are a circular strand of deoxyribonucleic acids with a partially complementary, anti-parallel base sequence.

A further feature or aspect of an embodiment is believed at the time of the filing of this patent application to possibly reside broadly in a DNA expression construct containing one or more coding nucleic acid sequences leading to expression of the *Leishmania infantum* antigens thiol-specific antioxidant protein Gene (TSA), glycoprotein gp63 and kinetoplastid membrane protein 11 (Kmp-11) or alleles or derivates thereof with corresponding functions.

Another feature or aspect of an embodiment is believed at the time of the filing of this patent application to possibly reside broadly in a DNA expression construct where the gene products or alleles or derivates thereof with corresponding function are expressed as single fusion protein.

Yet another feature or aspect of an embodiment is believed at the time of the filing of this patent application to possibly reside broadly in a DNA expression construct containing one or more coding nucleic acid sequences leading to expression of the *Leishmania infantum* antigens thiol-specific antioxidant protein Gene (TSA) and kinetoplastid membrane protein 11 (Kmp-11) or alleles or derivates thereof with corresponding functions.

Still another feature or aspect of an embodiment is believed at the time of the filing of this patent application to possibly reside broadly in a DNA expression construct where the gene products or alleles or derivates with corresponding function are expressed as single fusion protein.

A further feature or aspect of an embodiment is believed at the time of the filing of this patent application to possibly reside broadly in a DNA expression construct where the expression construct is a covalently closed linear deoxyribonucleic acid molecule, which comprise a linear double stranded region, the single strands forming said double stranded region being linked by short single stranded loops of deoxyribonucleic acid nucleotides, where the double strand forming single strands consist only of a coding sequence under control of a promoter sequence operable in the animal that is to be vaccinated and a terminator sequence.

Another feature or aspect of an embodiment is believed at the time of the filing of this patent application to possibly reside broadly in a DNA expression construct where the coding polynucleotide sequences are present as circular double stranded expression vectors.

Yet another feature or aspect of an embodiment is believed at the time of the filing of this patent application to possibly reside broadly in a DNA expression construct where the DNA expression construct is covalently linked to one or more oligopeptids to increase transfection efficiency.

Still another feature or aspect of an embodiment is believed at the time of the filing of this patent application to possibly reside broadly in a DNA expression construct where the DNA expression construct is linked to an oligopeptide of 3 to 30 amino acids, where the oligopeptide consists half of basic amino acids selected from the groups arginine and lysine.

A further feature or aspect of an embodiment is believed at the time of the filing of this patent application to possibly reside broadly in a DNA expression construct where the linked oligopeptide has the amino acid sequence YGRKKRRQRRR.

Another feature or aspect of an embodiment is believed at the time of the filing of this patent application to possibly reside broadly in a DNA expression construct where the linear covalently closed DNA expression construct is modified with a peptide containing the nuclear localisation sequence (NLS) of large T-antigen from SV40 PKKKRKV.

Yet another feature or aspect of an embodiment is believed at the time of the filing of this patent application to possibly reside broadly in a DNA expression construct where the sequence of gp63 is codon optimized.

Still another feature or aspect of an embodiment is believed at the time of the filing of this patent application to possibly reside broadly in a DNA expression construct containing the sequence Seq. ID 5.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the International Search Report dated Feb. 15, 2005, and/or cited elsewhere are hereby incorporated by reference as if set forth in their entirety herein as follows: WO 03/031469 A, published Apr. 17, 2003; WO 02/098359 A, published Dec. 12, 2002; All of the patents, patent applications or patent publications, which were cited in the International Search Report dated Feb. 15, 2005, and/or cited elsewhere are hereby incorporated by reference as if set forth in their entirety herein as follows: WO 03/031469 A, published Apr. 17, 2003; WO 02/098359 A, published Dec. 12, 2002; article entitled "DNA vaccination with linear minimalistic (MIDGE) vectors confers protection against *Leishmania* major infection in mice" published Dec. 13, 2002; article entitled "Protective efficacy of a tandemly linked, multi-subunit recombinant leishmanial vaccine (Leish-111f) formulated in MPL adjuvant" published Sep. 10, 2002; article entitled "Optimization of DNA vaccination against cutaneous leishmaniasis" published Nov. 1, 2002; article entitled "Attenuated *Toxoplasma gondii* ts-4 mutants engineered to express the *Leishmania* antigen KMP-11 elicit a specific immune response in BALB/c mice" published Nov. 12, 2001; and article entitled "Bacterial lipoprotein-based vaccines induce tumor necrosis factor-dependent type 1 protective immunity against *Leishmania* major" published January 2002.

The corresponding foreign and international patent publication applications, namely, European Patent Application No. 03090368.6, filed on Oct. 24, 2003, having inventors Burghardt Wittig, Laura Fuertes-López, and Marcos Timón-Jiménez, and International Application No. PCT/DE2004/002383, filed on Oct. 22, 2004, having WIPO Publication No. WO 2005/039633 A1, and inventors Burghardt Wittig, Laura Fuertes-López, and Marcos Timón-Jiménez, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in Europe and elsewhere, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The following U.S. Patents and Patent Applications are hereby incorporated by reference as if set forth in their entirety herein: U.S. Pat. No. 6,451,563, issued on Sep. 17, 2002; U.S. Pat. No. 6,451,593, issued on Sep. 17, 2002; U.S.

Pat. No. 6,849,725, issued on Feb. 1, 2005; U.S. patent application Ser. No. 10/528,748, filed on Mar. 22, 2005; U.S. patent application Ser. No. 10/816,465, filed on Apr. 1, 2004; and U.S. patent application Ser. No. 10/816,591, filed on Apr. 1, 2004.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b): "A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims." Therefore, any statements made relating to the abstract are not intended to limit the claims in any manner and should not be interpreted as limiting the claims in any manner.

The embodiments described herein above in the context of the preferred embodiments are not to be taken as limiting the embodiments to all of the provided details thereof, since modifications and variations thereof may be made without departing from the spirit and scope of the embodiments.

What is claimed is:

1. A DNA expression construct comprising a promoter sequence, a nucleic acid sequence which encodes a glycoprotein gp63, wherein said nucleic acid sequence comprises SEQ ID NO 5, and a termination sequence.

2. A DNA expression construct comprising the nucleic acid sequence SEQ ID NO 5 that encodes, upon expression in a cell, a fusion protein comprising glycoprotein gp63 and at least one of the following *Leishmania infantum* antigens: (i) thiol-specific antioxidant protein (TSA) and (ii) kinetoplastid membrane protein 11 (Kmp-11), wherein said DNA expression construct further comprises a promoter sequence and a termination sequence, wherein the promoter sequence and the termination sequence are operatively linked to the nucleic acid sequence, wherein said DNA expression construct is operable in a subject that is to be treated.

3. The construct of claim 2, wherein the subject is an animal.

* * * * *

SEQUENCE LISTING

<160> NUMBER OF SEQ ID NOS: 36

<210> SEQ ID NO 1
<211> LENGTH: 279
<212> TYPE: DNA
<213> ORGANISM: Leishmania infantum
<220> FEATURE:
<221> NAME/KEY: misc_feature
<223> OTHER INFORMATION: DNA sequence of Leishmania infantum
      kinetoplastid membrane protein 11 gene (Kmp-11)

<400> SEQUENCE: 1
atggccacca cgtacgagga gttttcggcg aagctggacc gcctggatga ggagttcaac      60
aggaagatgc aggagcagaa cgccaagttc tttgcggaca agccggatga gtcgacgctg     120
tcgcccgaga tgaaggagca ctacgagaag ttcgagcgca tgatcaagga acacacagag     180
aagttcaaca agaagatgca cgagcactcg gagcacttca agcagaagtt cgccgagctg     240
ctcgagcagc agaaggctgc gcagtaccca tccaagtaa                            279

<210> SEQ ID NO 2
<211> LENGTH: 92
<212> TYPE: PRT
<213> ORGANISM: Leishmania infantum
<220> FEATURE:
<221> NAME/KEY: MISC_FEATURE
<223> OTHER INFORMATION: Protein sequence of Leishmania infantum
      kinetoplastid membrane protein 11 antigen (Kmp-11)

<400> SEQUENCE: 2

Met Ala Thr Thr Tyr Glu Glu Phe Ser Ala Lys Leu Asp Arg Leu Asp
1               5                   10                  15

Glu Glu Phe Asn Arg Lys Met Gln Glu Gln Asn Ala Lys Phe Phe Ala
            20                  25                  30

Asp Lys Pro Asp Glu Ser Thr Leu Ser Pro Glu Met Lys Glu His Tyr
        35                  40                  45

Glu Lys Phe Glu Arg Met Ile Lys Glu His Thr Glu Lys Phe Asn Lys
    50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys
                85                  90

<210> SEQ ID NO 3
<211> LENGTH: 600
<212> TYPE: DNA
<213> ORGANISM: Leishmania infantum
<220> FEATURE:
<221> NAME/KEY: misc_feature
<223> OTHER INFORMATION: DNA sequence of Leishmania infantum
      thiol-specific antioxidant protein gene (TSA)

<400> SEQUENCE: 3

```
atgtcctgcg gtaacgccaa gatcaactgt cccgcgccgc ccttcgagga ggtggcgctc      60
atgcccaacg gcagcttcaa gaagatcagc ctcgccgcct acaagggcaa gtgggtcgtg     120
ctcttcttct acccgctcga cttcaccttc gtgtgcccga cagagatcat cgcgttctcc     180
gaaaacgtga gtcgcttcaa cgagctcaac tgcgaggtcc tcgcgtgctc catggacagc     240
gagtacgcgc acctgcagtg gacgctgcag gaccgcaaga agggcggcct cggcgccatg     300
gcgattccaa tgctggccga caagaccaag agtatcgctc gtgcctacgg cgtgctggag     360
gagaaacagg gcgtggccta ccgcggtcta ttcatcatcg accccaatgg catggtgcgc     420
cagatcaccg tcaacgacat gccggtgggc cgcaacgtgg aggaggttct gcgcctgctg     480
gaggcttttc agttcgtgga gaagcacggc gaggtgtgcc ccgcgaactg gaagaagggc     540
gcccccacga tgaagccgga gccgaaggcg tctgtcgaag gatacttcag caagcagtaa     600
```

<210> SEQ ID NO 4
<211> LENGTH: 199
<212> TYPE: PRT
<213> ORGANISM: Leishmania infantum
<220> FEATURE:
<221> NAME/KEY: MISC_FEATURE
<223> OTHER INFORMATION: Protein sequence of Leishmania infantum
      thiol-specific antioxidant protein antigen (TSA)

<400> SEQUENCE: 4

```
Met Ser Cys Gly Asn Ala Lys Ile Asn Cys Pro Ala Pro Phe Glu
1               5                   10                  15

Glu Val Ala Leu Met Pro Asn Gly Ser Phe Lys Lys Ile Ser Leu Ala
            20                  25                  30

Ala Tyr Lys Gly Lys Trp Val Val Leu Phe Phe Tyr Pro Leu Asp Phe
        35                  40                  45

Thr Phe Val Cys Pro Thr Glu Ile Ile Ala Phe Ser Glu Asn Val Ser
    50                  55                  60

Arg Phe Asn Glu Leu Asn Cys Glu Val Leu Ala Cys Ser Met Asp Ser
65                  70                  75                  80

Glu Tyr Ala His Leu Gln Trp Thr Leu Gln Asp Arg Lys Lys Gly Gly
                85                  90                  95

Leu Gly Ala Met Ala Ile Pro Met Leu Ala Asp Lys Thr Lys Ser Ile
            100                 105                 110

Ala Arg Ala Tyr Gly Val Leu Glu Glu Lys Gln Gly Val Ala Tyr Arg
        115                 120                 125

Gly Leu Phe Ile Ile Asp Pro Asn Gly Met Val Arg Gln Ile Thr Val
    130                 135                 140

Asn Asp Met Pro Val Gly Arg Asn Val Glu Glu Val Leu Arg Leu Leu
145                 150                 155                 160

Glu Ala Phe Gln Phe Val Glu Lys His Gly Glu Val Cys Pro Ala Asn
                165                 170                 175
```

Trp Lys Lys Gly Ala Pro Thr Met Lys Pro Glu Pro Lys Ala Ser Val
            180                 185                 190

Glu Gly Tyr Phe Ser Lys Gln
        195

<210> SEQ ID NO 5
<211> LENGTH: 1800
<212> TYPE: DNA
<213> ORGANISM: Artificial Sequence
<220> FEATURE:
<223> OTHER INFORMATION: DNA sequence of codon-optimized Leishmania
      infantum Antigen gp63

<400> SEQUENCE: 5

| | | | | | |
|---|---|---|---|---|---|
| atgtctgtgg | actcctcctc | cacccacaga | cacagatctg | tggctgccag | actggtgaga | 60 |
| ctggctgcag | ctggagctgc | tgtgattgct | gctgtgggca | cagctgctgc | ctgggcccat | 120 |
| gctggagctg | tgcagcacag | atgcatccat | gatgccatgc | aggccagagt | gagacagtct | 180 |
| gtggccagac | accacacagc | cccaggagct | gtgtctgctg | tgggcctgcc | ctatgtgacc | 240 |
| ctggacacag | ctgcagctgc | agacagaaga | ccaggctctg | ccccacagt | ggtgagagct | 300 |
| gccaactggg | agccctgag | gattgctgtg | tccacagagg | acctgacaga | cccagcctac | 360 |
| cactgtgcca | gagtgggcca | gcacatcaag | agaagactgg | gaggagtgga | catctgcaca | 420 |
| gctgaggaca | tcctgacaga | tgagaagaga | gacatcctgg | tgaagcacct | gatccccag | 480 |
| gccctgcagc | tgcacacaga | gagactgaaa | gtgagacagg | tgcaggacaa | gtggaaggtg | 540 |
| acaggcatgg | agatgatgt | gtgctctgac | ttcaaggtgc | cccagccca | catcacagat | 600 |
| ggcctgtcca | acacagactt | tgtgatgtat | gtgacctctg | tgccctctga | ggagggagtg | 660 |
| ctggcctggg | ccaccatctg | ccaggtgttc | tctgatggcc | acccaaccgt | gggagtgatc | 720 |
| aacatcccag | ctgccaacat | tgcctccaga | tatgaccagc | tggtgaccag | agtggtgacc | 780 |
| catgagatgg | cccatgccct | gggcttctct | gtgggcttct | ttgagggagc | agaatcctg | 840 |
| gagtccatct | ccaatgtgag | acacaaggac | tttgatgtgc | cagtgatcaa | ctcctccact | 900 |
| gctgtggcca | aggccagaga | gcagtatggc | tgtgacaccc | tggagtacct | ggagattgag | 960 |
| gaccagggag | agctggctc | tgctggctcc | cacatcaaga | tgagaaatgc | caggatgag | 1020 |
| ctgatggccc | cagctgcagc | tgcaggctac | tactctgccc | tgaccacggc | catcttccag | 1080 |
| gacctgggct | tctaccaggc | tgacttctcc | aaggctgagg | tgatgccctg | gggcagaaat | 1140 |
| gctggctgtg | ccttcctgtc | tgagaagtgc | atggagagaa | acatcaccga | gtggccagcc | 1200 |
| atgttctgca | atgagaatga | ggtgaccatg | agatgcccca | cctccagact | gtccctgggc | 1260 |
| aagtgtggag | tgaccagaca | cccagacctg | cccccctact | ggcagtactt | cacagacccc | 1320 |
| tccctggctg | gcatctctgc | cttcatggac | tgctgcccag | tgcggagcc | ctatggagat | 1380 |
| ggctcctgtg | cccagagagc | ctctgaggct | ggagccccct | tcaagggctt | caatgtgttc | 1440 |
| tctgatgctg | cccgatgcat | tgatggagcc | ttcagaccca | agacctccca | tggcatcatc | 1500 |
| aagtcctatg | ctggcctgtg | tgccaatgtg | agatgtgaca | cagccaccag | aacctactct | 1560 |
| gtgcaggtgc | atggaggctc | tggctatgcc | aactgcaccc | caggcctgag | agtggagctg | 1620 |
| tccacagtgt | cctctgcctt | tgaggaggga | ggctacatca | cctgccccc | ctatgtggag | 1680 |
| gtgtgccagg | caatgtgca | ggctgccaag | gatggaggca | atgcagctgc | tggcagaaga | 1740 |
| ggccccagag | ctgctgccac | agccctgctg | gtggctgccc | tgctggctgt | ggccctgtag | 1800 |

<210> SEQ ID NO 6
<211> LENGTH: 599
<212> TYPE: PRT
<213> ORGANISM: Artificial Sequence
<220> FEATURE:
<223> OTHER INFORMATION: Protein sequence of codon-optimized Leishmania
      infantum Antigen gp63

<400> SEQUENCE: 6

```
Met Ser Val Asp Ser Ser Thr His Arg His Arg Ser Val Ala Ala
1               5                   10                  15

Arg Leu Val Arg Leu Ala Ala Gly Ala Ala Val Ile Ala Ala Val
                20                  25                  30

Gly Thr Ala Ala Ala Trp Ala His Ala Gly Ala Val Gln His Arg Cys
            35                  40                  45

Ile His Asp Ala Met Gln Ala Arg Val Arg Gln Ser Val Ala Arg His
        50                  55                  60

His Thr Ala Pro Gly Ala Val Ser Ala Val Gly Leu Pro Tyr Val Thr
65                  70                  75                  80

Leu Asp Thr Ala Ala Ala Asp Arg Arg Pro Gly Ser Ala Pro Thr
                85                  90                  95

Val Val Arg Ala Ala Asn Trp Gly Ala Leu Arg Ile Ala Val Ser Thr
                100                 105                 110

Glu Asp Leu Thr Asp Pro Ala Tyr His Cys Ala Arg Val Gly Gln His
                115                 120                 125

Ile Lys Arg Arg Leu Gly Gly Val Asp Ile Cys Thr Ala Glu Asp Ile
        130                 135                 140

Leu Thr Asp Glu Lys Arg Asp Ile Leu Val Lys His Leu Ile Pro Gln
145                 150                 155                 160

Ala Leu Gln Leu His Thr Glu Arg Leu Lys Val Arg Gln Val Gln Asp
                165                 170                 175

Lys Trp Lys Val Thr Gly Met Gly Asp Asp Val Cys Ser Asp Phe Lys
                180                 185                 190

Val Pro Pro Ala His Ile Thr Asp Gly Leu Ser Asn Thr Asp Phe Val
                195                 200                 205

Met Tyr Val Thr Ser Val Pro Ser Glu Glu Gly Val Leu Ala Trp Ala
        210                 215                 220

Thr Ile Cys Gln Val Phe Ser Asp Gly His Pro Thr Val Gly Val Ile
225                 230                 235                 240

Asn Ile Pro Ala Ala Asn Ile Ala Ser Arg Tyr Asp Gln Leu Val Thr
                245                 250                 255

Arg Val Val Thr His Glu Met Ala His Ala Leu Gly Phe Ser Val Gly
                260                 265                 270

Phe Phe Glu Gly Ala Arg Ile Leu Glu Ser Ile Ser Asn Val Arg His
            275                 280                 285

Lys Asp Phe Asp Val Pro Val Ile Asn Ser Ser Thr Ala Val Ala Lys
        290                 295                 300

Ala Arg Glu Gln Tyr Gly Cys Asp Thr Leu Glu Tyr Leu Glu Ile Glu
305                 310                 315                 320

Asp Gln Gly Gly Ala Gly Ser Ala Gly Ser His Ile Lys Met Arg Asn
                325                 330                 335

Ala Gln Asp Glu Leu Met Ala Pro Ala Ala Ala Gly Tyr Tyr Ser
                340                 345                 350

Ala Leu Thr Thr Ala Ile Phe Gln Asp Leu Gly Phe Tyr Gln Ala Asp
        355                 360                 365
```

```
Phe Ser Lys Ala Glu Val Met Pro Trp Gly Arg Asn Ala Gly Cys Ala
    370                 375                 380

Phe Leu Ser Glu Lys Cys Met Glu Arg Asn Ile Thr Glu Trp Pro Ala
385                 390                 395                 400

Met Phe Cys Asn Glu Asn Glu Val Thr Met Arg Cys Pro Thr Ser Arg
                405                 410                 415

Leu Ser Leu Gly Lys Cys Gly Val Thr Arg His Pro Asp Leu Pro Pro
                420                 425                 430

Tyr Trp Gln Tyr Phe Thr Asp Pro Ser Leu Ala Gly Ile Ser Ala Phe
            435                 440                 445

Met Asp Cys Cys Pro Val Ala Glu Pro Tyr Gly Asp Gly Ser Cys Ala
    450                 455                 460

Gln Arg Ala Ser Glu Ala Gly Ala Pro Phe Lys Gly Phe Asn Val Phe
465                 470                 475                 480

Ser Asp Ala Ala Arg Cys Ile Asp Gly Ala Phe Arg Pro Lys Thr Ser
                485                 490                 495

His Gly Ile Ile Lys Ser Tyr Ala Gly Leu Cys Ala Asn Val Arg Cys
                500                 505                 510

Asp Thr Ala Thr Arg Thr Tyr Ser Val Gln Val His Gly Gly Ser Gly
            515                 520                 525

Tyr Ala Asn Cys Thr Pro Gly Leu Arg Val Glu Leu Ser Thr Val Ser
    530                 535                 540

Ser Ala Phe Glu Glu Gly Gly Tyr Ile Thr Cys Pro Pro Tyr Val Glu
545                 550                 555                 560

Val Cys Gln Gly Asn Val Gln Ala Ala Lys Asp Gly Gly Asn Ala Ala
                565                 570                 575

Ala Gly Arg Arg Gly Pro Arg Ala Ala Thr Ala Leu Leu Val Ala
            580                 585                 590

Ala Leu Leu Ala Val Ala Leu
        595

<210> SEQ ID NO 7
<211> LENGTH: 939
<212> TYPE: DNA
<213> ORGANISM: Leishmania infantum
<220> FEATURE:
<221> NAME/KEY: misc_feature
<223> OTHER INFORMATION: DNA sequence of Leishmania infantum antigen p36
      (LACK)

<400> SEQUENCE: 7
atgaactacg agggtcacct gaagggccac cgcggatggg tcacctccct ggcctgcccg      60
cagcaggcgg ggtcgtacat caaggtggtg tcgacgtcgc gcgatggcac ggccatctcg     120
tggaaagcca accccgaccg ccacagcgtg gacagcgact acggtctgcc gagccaccgc     180
ctcgagggcc acaccggctt cgtgtcgtgt gtgtcgctgg cccacgccac cgactacgcg     240
ctgaccgcgt cctgggaccg ctccatccgc atgtgggacc tgcgcaatgg ccagtgccag     300
cgcaagttcc tgaagcacac caaggacgtg ctcgccgtcg ccttctcgcc ggacgaccgc     360
ctgatcgtgt ccgcgggccg cgacaacgtg atccgcgtgt ggaacgtggc gggcgagtgc     420
atgcacgagt cctgcgcgga cggccacgag gactgggtga gcagcatctg tttctcgccg     480
tcgctggagc atccgatcgt ggtgtccggc agctgggaca cacaccatca aggtatggaac    540 gtgaacgggg gcaagtgtga gcgcacgctc aaggccaca gcaactacgt gtccacggtg      600
acggtgtcgc cagacgggtc gctgtgcgcg tccggcggca aggacggcgc ggcgctgctg     660
```

-continued

```
tgggacctga gcaccggcga gcagctgttc aagatcaacg tggagtcgcc catcaaccag    720
atcgccttct cgcccaaccg cttctggatg tgcgtcgcga cggagaggtc cctgtccgtg    780
tacgacctgg agagcaaggc tgtgattgcg gagctgacgc cggacggcgc gaagccgtcc    840
gagtgcatct ccattgcctg gtccgccgac ggcaacactc tgtactccgg tcacaaggac    900
aacctgatcc gcgtgtggtc catctccgac gccgagtaa                           939
```

<210> SEQ ID NO 8
<211> LENGTH: 312
<212> TYPE: PRT
<213> ORGANISM: Leishmania infantum
<220> FEATURE:
<221> NAME/KEY: MISC_FEATURE
<223> OTHER INFORMATION: Protein sequence of Leishmania infantum antigen
    p36 (LACK)

<400> SEQUENCE: 8

```
Met Asn Tyr Glu Gly His Leu Lys Gly His Arg Gly Trp Val Thr Ser
1               5                   10                  15

Leu Ala Cys Pro Gln Gln Ala Gly Ser Tyr Ile Lys Val Val Ser Thr
            20                  25                  30

Ser Arg Asp Gly Thr Ala Ile Ser Trp Lys Ala Asn Pro Asp Arg His
        35                  40                  45

Ser Val Asp Ser Asp Tyr Gly Leu Pro Ser His Arg Leu Glu Gly His
    50                  55                  60

Thr Gly Phe Val Ser Cys Val Ser Leu Ala His Ala Thr Asp Tyr Ala
65                  70                  75                  80

Leu Thr Ala Ser Trp Asp Arg Ser Ile Arg Met Trp Asp Leu Arg Asn
                85                  90                  95

Gly Gln Cys Gln Arg Lys Phe Leu Lys His Thr Lys Asp Val Leu Ala
            100                 105                 110

Val Ala Phe Ser Pro Asp Asp Arg Leu Ile Val Ser Ala Gly Arg Asp
        115                 120                 125

Asn Val Ile Arg Val Trp Asn Val Ala Gly Glu Cys Met His Glu Phe
    130                 135                 140

Leu Arg Asp Gly His Glu Asp Trp Val Ser Ser Ile Cys Phe Ser Pro
145                 150                 155                 160

Ser Leu Glu His Pro Ile Val Val Ser Gly Ser Trp Asp Asn Thr Ile
                165                 170                 175

Lys Val Trp Asn Val Asn Gly Gly Lys Cys Glu Arg Thr Leu Lys Gly
            180                 185                 190

His Ser Asn Tyr Val Ser Thr Val Thr Val Ser Pro Asp Gly Ser Leu
        195                 200                 205

Cys Ala Ser Gly Gly Lys Asp Gly Ala Ala Leu Leu Trp Asp Leu Ser
    210                 215                 220

Thr Gly Glu Gln Leu Phe Lys Ile Asn Val Glu Ser Pro Ile Asn Gln
225                 230                 235                 240

Ile Ala Phe Ser Pro Asn Arg Phe Trp Met Cys Val Ala Thr Glu Arg
                245                 250                 255

Ser Leu Ser Val Tyr Asp Leu Glu Ser Lys Ala Val Ile Ala Glu Leu
            260                 265                 270

Thr Pro Asp Gly Ala Lys Pro Ser Glu Cys Ile Ser Ile Ala Trp Ser
        275                 280                 285
```

Ala Asp Gly Asn Thr Leu Tyr Ser Gly His Lys Asp Asn Leu Ile Arg
    290                 295                 300

Val Trp Ser Ile Ser Asp Ala Glu
305                 310

<210> SEQ ID NO 9
<211> LENGTH: 7
<212> TYPE: PRT
<213> ORGANISM: Simian virus 40
<220> FEATURE:
<221> NAME/KEY: MISC_FEATURE
<223> OTHER INFORMATION: Nuclear localization sequence

<400> SEQUENCE: 9

Pro Lys Lys Lys Arg Lys Val
1               5

<210> SEQ ID NO 10
<211> LENGTH: 11
<212> TYPE: PRT
<213> ORGANISM: Human immunodeficiency virus type 1
<220> FEATURE:
<221> NAME/KEY: MISC_FEATURE
<223> OTHER INFORMATION: Large T-peptide fragment of HIV-1 gene product
      TAT

<400> SEQUENCE: 10

Tyr Gly Arg Lys Lys Arg Arg Gln Arg Arg Arg
1               5                   10

<210> SEQ ID NO 11
<211> LENGTH: 33
<212> TYPE: DNA
<213> ORGANISM: Artificial Sequence
<220> FEATURE:
<223> OTHER INFORMATION: 1. PCR-Primer left; synthetic Oligo

<400> SEQUENCE: 11
ttatatggta ccatgaacat acgagggtca cct                                 33

<210> SEQ ID NO 12
<211> LENGTH: 42
<212> TYPE: DNA
<213> ORGANISM: Artificial Sequence
<220> FEATURE:
<223> OTHER INFORMATION: 1. PCR-Primer right; synthetic Oligo

<400> SEQUENCE: 12
ttatatgagc tcagaagaca cggacaggga cctcttccgt cg                       42

<210> SEQ ID NO 13
<211> LENGTH: 33
<212> TYPE: DNA
<213> ORGANISM: Artificial Sequence
<220> FEATURE:
<223> OTHER INFORMATION: 2. PCR-Primer left; synthetic Oligo

<400> SEQUENCE: 13
ttatatggta ccatgaacat acgagggtca cct                                 33

<210> SEQ ID NO 14
<211> LENGTH: 33
<212> TYPE: DNA
<213> ORGANISM: Artificial Sequence
<220> FEATURE:
<223> OTHER INFORMATION: 2.PCR-Primer right; synthetic Oligo

<400> SEQUENCE: 14
ttatatgagc tcttactcgg ccgtcggaga tgg                33

<210> SEQ ID NO 15
<211> LENGTH: 30
<212> TYPE: DNA
<213> ORGANISM: Artificial Sequence
<220> FEATURE:
<223> OTHER INFORMATION: Kmp-11 PCR-Primer left; synthetic Oligo

<400> SEQUENCE: 15
attataggta ccatggccac cacgtacgag                30

<210> SEQ ID NO 16
<211> LENGTH: 32
<212> TYPE: DNA
<213> ORGANISM: Artificial Sequence
<220> FEATURE:
<223> OTHER INFORMATION: Kmp-11 PCR-Primer right; synthetic Oligo

<400> SEQUENCE: 16
ttaattctcg agttacttgg atgggtactg cg                32

<210> SEQ ID NO 17
<211> LENGTH: 36
<212> TYPE: DNA
<213> ORGANISM: Artificial Sequence
<220> FEATURE:
<223> OTHER INFORMATION: TSA PCR-Primer left; synthetic Oligo

<400> SEQUENCE: 17
aattatggta ccatgtcctg cggtaacgcc aagatc                36

<210> SEQ ID NO 18
<211> LENGTH: 39
<212> TYPE: DNA
<213> ORGANISM: Artificial Sequence
<220> FEATURE:
<223> OTHER INFORMATION: TSA PCR-Primer right; synthetic Oligo

<400> SEQUENCE: 18
aatatactcg agttactgct tgctgaagta tccttcgac                39

<210> SEQ ID NO 19
<211> LENGTH: 22
<212> TYPE: DNA
<213> ORGANISM: Artificial Sequence
<220> FEATURE:
<223> OTHER INFORMATION: TSA left Mutation primer; synthetic Oligo

<400> SEQUENCE: 19
taccgcggtc tcttcatcat cg                22

<210> SEQ ID NO 20
<211> LENGTH: 32
<212> TYPE: DNA
<213> ORGANISM: Artificial Sequence
<220> FEATURE:
<223> OTHER INFORMATION: TSA right Mutation primer; synthetic Oligo

<400> SEQUENCE: 20
attgggggtc tcgatgaata gaccgcggta gg                32

<210> SEQ ID NO 21
<211> LENGTH: 25
<212> TYPE: DNA
<213> ORGANISM: Artificial Sequence
<220> FEATURE:
<223> OTHER INFORMATION: gp63 Fragment 1 left Primer; synthetic Oligo

<400> SEQUENCE: 21
attattggta ccatgtctgt ggact                                    25

<210> SEQ ID NO 22
<211> LENGTH: 31
<212> TYPE: DNA
<213> ORGANISM: Artificial Sequence
<220> FEATURE:
<223> OTHER INFORMATION: gp63 Fragment 1 right Primer; synthetic Oligo

<400> SEQUENCE: 22
ttatatggtc tctctcaggg ctccccagtt g                             31

<210> SEQ ID NO 23
<211> LENGTH: 36
<212> TYPE: DNA
<213> ORGANISM: Artificial Sequence
<220> FEATURE:
<223> OTHER INFORMATION: gp63 Fragment 2 left Primer; synthetic Oligo

<400> SEQUENCE: 23
attataggtc tcctgagaat tgctgtgtcc acagag                        36

<210> SEQ ID NO 24
<211> LENGTH: 34
<212> TYPE: DNA
<213> ORGANISM: Artificial Sequence
<220> FEATURE:
<223> OTHER INFORMATION: gp63 Fragment 2 right Primer; synthetic Oligo

<400> SEQUENCE: 24
ttatatggtc tcacagaggc cacatacatc acaa                          34

<210> SEQ ID NO 25
<211> LENGTH: 43
<212> TYPE: DNA
<213> ORGANISM: Artificial Sequence
<220> FEATURE:
<223> OTHER INFORMATION: gp63 Fragment 3 left Primer; synthetic Oligo

<400> SEQUENCE: 25
tattatggtc tcctctgtgc cctctgagga gggagtgctg gcc                43

<210> SEQ ID NO 26
<211> LENGTH: 34
<212> TYPE: DNA
<213> ORGANISM: Artificial Sequence
<220> FEATURE:
<223> OTHER INFORMATION: gp63 Fragment 3 right Primer; synthetic Oligo

<400> SEQUENCE: 26
aattatggtc tcctcaatct ccaggtactc cagg                          34

<210> SEQ ID NO 27
<211> LENGTH: 31
<212> TYPE: DNA
<213> ORGANISM: Artificial Sequence
<220> FEATURE:
<223> OTHER INFORMATION: gp63 Fragment 4 left Primer; synthetic Oligo

```
<400> SEQUENCE: 27
attataggtc tcattgagga ccagggagga g                            31

<210> SEQ ID NO 28
<211> LENGTH: 34
<212> TYPE: DNA
<213> ORGANISM: Artificial Sequence
<220> FEATURE:
<223> OTHER INFORMATION: gp63 Fragment 4 right Primer; synthetic Oligo

<400> SEQUENCE: 28
taatatggtc tcgtgtctgg tcactccaca cttg                         34

<210> SEQ ID NO 29
<211> LENGTH: 31
<212> TYPE: DNA
<213> ORGANISM: Artificial Sequence
<220> FEATURE:
<223> OTHER INFORMATION: gp63 Fragment 5 left Primer; synthetic Oligo

<400> SEQUENCE: 29
attataggtc tcagacaccc agacctgccc c                            31

<210> SEQ ID NO 30
<211> LENGTH: 32
<212> TYPE: DNA
<213> ORGANISM: Artificial Sequence
<220> FEATURE:
<223> OTHER INFORMATION: gp63 Fragment 5 right Primer; synthetic Oligo

<400> SEQUENCE: 30
ttatatggtc tcggggtgca gttggcatag cc                           32

<210> SEQ ID NO 31
<211> LENGTH: 32
<212> TYPE: DNA
<213> ORGANISM: Artificial Sequence
<220> FEATURE:
<223> OTHER INFORMATION: gp63 Fragment 6 left Primer; synthetic Oligo

<400> SEQUENCE: 31
atatatggtc tccaccccag gcctgagagt gg                           32

<210> SEQ ID NO 32
<211> LENGTH: 34
<212> TYPE: DNA
<213> ORGANISM: Artificial Sequence
<220> FEATURE:
<223> OTHER INFORMATION: gp63 Fragment 6 right Primer; synthetic Oligo

<400> SEQUENCE: 32
taatatgagc tcctacaggg ccacagccag cagg                         34

<210> SEQ ID NO 33
<211> LENGTH: 25
<212> TYPE: DNA
<213> ORGANISM: Artificial Sequence
<220> FEATURE:
<223> OTHER INFORMATION: gp63 Whole sequence left Primer; synthetic
      Oligo

<400> SEQUENCE: 33
attattggta ccatgtctgt ggact                                   25
```

-continued

```
<210> SEQ ID NO 34
<211> LENGTH: 34
<212> TYPE: DNA
<213> ORGANISM: Artificial Sequence
<220> FEATURE:
<223> OTHER INFORMATION: gp63 Whole sequence right Primer; synthetic
      Oligo

<400> SEQUENCE: 34
taatatgagc tcctacaggg ccacagccag cagg                              34

<210> SEQ ID NO 35
<211> LENGTH: 20
<212> TYPE: DNA
<213> ORGANISM: Artificial Sequence
<220> FEATURE:
<223> OTHER INFORMATION: ODN1; synthetic Oligo
<220> FEATURE:
<221> NAME/KEY: misc_feature
<222> LOCATION: (12)..(12)
<223> OTHER INFORMATION: T = chemically modified Thymin

<400> SEQUENCE: 35
gggagtccag ttttctggac                                              20

<210> SEQ ID NO 36
<211> LENGTH: 20
<212> TYPE: DNA
<213> ORGANISM: Artificial Sequence
<220> FEATURE:
<223> OTHER INFORMATION: ODN 2; synthetic Oligo

<400> SEQUENCE: 36
aggggtccag ttttctggac                                              20
```